(12) United States Patent
Connolly et al.

(10) Patent No.: US 10,094,818 B2
(45) Date of Patent: Oct. 9, 2018

(54) BACTERIAL/CELLULAR RECOGNITION IMPEDANCE ALGORITHM

(75) Inventors: Patricia Connolly, Glasgow (GB); Laurie Shedden, Glasgow (GB)

(73) Assignee: University of Strathclyde, Glasgow (GB)

( * ) Notice: Subject to any disclaimer, the term of this patent is extended or adjusted under 35 U.S.C. 154(b) by 1314 days.

(21) Appl. No.: 12/990,921

(22) PCT Filed: May 7, 2009

(86) PCT No.: PCT/GB2009/001132
§ 371 (c)(1),
(2), (4) Date: Jan. 26, 2011

(87) PCT Pub. No.: WO2009/136157
PCT Pub. Date: Nov. 12, 2009

(65) Prior Publication Data
US 2011/0144469 A1    Jun. 16, 2011

(30) Foreign Application Priority Data

May 7, 2008   (GB) .................................... 0808266.1
Apr. 17, 2009  (GB) .................................... 0906653.1

(51) Int. Cl.
G01N 33/487    (2006.01)
A61B 5/053     (2006.01)
(Continued)

(52) U.S. Cl.
CPC ..... *G01N 33/48735* (2013.01); *A61B 5/0531* (2013.01); *A61B 5/0538* (2013.01);
(Continued)

(58) Field of Classification Search
CPC ..... A61B 5/053; A61B 5/0531–5/0538; A61B 5/14532; G01N 33/5005; G01N 33/5091; G01N 33/5094
(Continued)

(56) References Cited

U.S. PATENT DOCUMENTS 6,716,620 B2 * 4/2004 Bashir .............. G01N 33/56911
                                              435/287.1
7,459,303 B2   12/2008 Wang et al.
(Continued)

FOREIGN PATENT DOCUMENTS

JP    2005-537498 A    12/2005
WO   WO 00/22431 A1   4/2000
(Continued)

OTHER PUBLICATIONS

Lind, R. et al., *Single Cell Mobility and Adhesion Monitoring Using Extracellular Electrodes*, Biosensors & Bioelectronics, 6, (1991), pp. 359-367.
(Continued)

*Primary Examiner* — Adam J Eiseman
(74) *Attorney, Agent, or Firm* — Alston & Bird LLP

(57) ABSTRACT

A method for characterising cells or cell structures in a sample comprising: obtaining at least one normalized impedance response of the sample over at least one frequency range; and characterising at least one cell using at least one characteristic of the normalized impedance response.

23 Claims, 4 Drawing Sheets

(51) Int. Cl.
*A61B 5/1468* (2006.01)
*A61B 5/1473* (2006.01)
*A61B 5/00* (2006.01)
*C12M 1/34* (2006.01)
*G01N 27/02* (2006.01)

(52) U.S. Cl.
CPC .......... *A61B 5/1468* (2013.01); *A61B 5/1473* (2013.01); *A61B 5/445* (2013.01); *A61B 5/6862* (2013.01); *C12M 41/36* (2013.01); *G01N 27/026* (2013.01)

(58) Field of Classification Search
USPC ........................................................ 600/547
See application file for complete search history.

(56) References Cited

U.S. PATENT DOCUMENTS

| 2003/0149368 | A1  | 8/2003  | Hennemann et al. | |
|---|---|---|---|---|
| 2003/0158584 | A1  | 8/2003  | Cates et al. | |
| 2005/0153425 | A1* | 7/2005  | Xu et al. | 435/287.1 |
| 2006/0235286 | A1  | 10/2006 | Stone et al. | |
| 2015/0265191 | A1* | 9/2015  | Harding | A61B 5/14539 600/361 |

FOREIGN PATENT DOCUMENTS

| WO | WO-2004/010103 A2 | 1/2004 |
|---|---|---|
| WO | WO 2006/105121 A2 | 10/2006 |
| WO | WO 2008/042673 A1 | 4/2008 |

OTHER PUBLICATIONS

Rothermel, A. et al., *Real-Time Management of PMA-Induced Cellular Alterations by Microelectrode Array-Based Impedance Spectroscopy*, Short Technical Reports, BioTechniques, vol. 41, No. 4, (2006), pp. 445-450.

Varshney, M. et al., *Interdigitated Array Microelectrode Based Impedance Biosensor Coupled With Magnetic Nanoparticle-Antibody Conjugates for Detection of Escherichia coli O157:H7 in Food Samples*, Biosensor and Bioelectronics, 22, (2007), pp. 2048-2414.

International Search Report for Application No. PCT/GB2009/001132 dated Dec. 11, 2009.

International Preliminary Report on Patentability for Application No. PCT/GB2009/001132 dated May 21, 2010.

Search Report for Application No. GB0808266.1 dated Aug. 7, 2008.

* cited by examiner

BACTERIAL/CELLULAR RECOGNITION IMPEDANCE ALGORITHM

The present invention relates to a system and method for characterising cells and structures formed from cells.

BACKGROUND OF THE INVENTION

Various techniques have been reported for monitoring growth or other characteristics of biological cells. One such technique involves the use of impedance methods, as reported by Lind R et. al. in "Single Cell Mobility and Adhesion Monitoring Using Extracellular Electrodes", Biosensors and Bioelectronics, 6 (4), pp 359-367, 1991. Other reported techniques involve determining changes in impedance and linking these to cell or bacterial growth or movement.

Most of these techniques involve measuring ac impedance of cells or bacteria in their appropriate growth media. A good degree of success has been achieved in using these methods to link overall changes in impedance, Z, at some fixed electrical stimulating frequency, typically in the kilohertz range, to the growth of cells and bacteria. However, the use of impedance techniques for monitoring growth or other characteristics of biological cells is complicated by the fact that each measuring system has its own characteristic impedance, which must be separated from the impedance response of the cells.

SUMMARY OF INVENTION

According to a first aspect of the present invention, there is provided a method for characterising cells or cell structures in a sample comprising: obtaining at least one normalized impedance response of the sample over at least one frequency range; and characterising at least one cell using at least one characteristic of the normalized impedance response.

By monitoring the frequency response of normalised impedance over a spectrum of frequencies, it has been found that characteristic features in the frequency response of normalised impedance may be identified and used to classify cells in a consistent and repeatable manner. The use of normalised impedance has the further advantage that there is no need to continuously separately characterise the electrodes. Furthermore, the AC impedance technique is quick, simple and removing the need for constant recalibration allows continual monitoring of cell cultures.

The frequency range may be a continuous or quasi-continuous frequency range or spectrum. The frequency range may comprise a series of discrete frequency measurements. The frequency range may be any frequency range lying between 0.1 Hz and 33 MHz.

The method may include providing a system having at least two electrodes. The sample may be provided in an electrical path between the electrodes.

The at least one cell may be a bacteria or other single cell organism. The at least one cell may be a plant or animal cell such as a plant or animal tissue cell. At least one cell may be arranged in a structure, which may be plant or animal tissue or a multi-cell organism.

The method may comprise obtaining a baseline impedance response of the system over the at least one frequency range.

The baseline impedance response may be obtained by measuring the impedance response of the system over the frequency range with substantially no cells in an electrical path between the electrodes.

The baseline impedance response may be an initial or a calculated or estimated or standard impedance response of the system. The baseline impedance response may be obtained by measuring the impedance response of a similar and/or standardised system over the at least one frequency range with substantially no cells in an electrical path between the electrodes.

The method may comprise obtaining at least one measured impedance response of the system over the at least one frequency range.

The at least one measured impedance response of the system over the at least one frequency range may be obtained after introduction and/or growth of at least one cell in the electrical path between the electrodes.

Obtaining the at least one normalized impedance response may comprise dividing the at least one measured impedance response of the system at each frequency in the frequency range by the baseline impedance response of the system for the corresponding frequency.

The at least one characteristic of the normalized impedance response may be frequency dependent. The at least one characteristic of the normalized impedance response may be the frequency and/or the peak size and/or peak shape of at least one peak in the normalized impedance response over the frequency range. Multiple peaks may be observed in the normalised impedance. The peak or peaks may be dependent upon cell or bacterial activity. Such single or multiple peaks may be used to determine the stage of growth of a cell or bacterial system. Changes in at least one peak obtained in the normalised system may be tracked over time to allow the distinction of changes in cell or bacterial growth.

The at least one peak in normalised impedance with frequency may be characteristic of cell or bacterial type and/or growth stage. Thus the normalised impedance may be used to determine the presence of a particular cell, bacteria, tissue type or molecular by product in the system.

The electrodes may be immersed in a culture medium. The culture medium may be arranged to promote the growth of at least one type of cells. The at least one cell may be contained within the medium. The at least one cell may be in contact with one or more of the electrodes.

The measurement of the impedance response of the system and/or the baseline impedance response of the system and/or the normalized impedance response of the system may be made using AC impedance techniques.

According to a second aspect of the present invention, there is provided a system for characterising cells or cell structures in a sample comprising: at least two electrodes coupled with a controller, the controller being adapted to obtain at least one normalized impedance response from the sample over a frequency range via the electrodes; and characterise at least one cell or cell structure using at least one characteristic of the normalized impedance response.

The controller may be arranged to determine impedance via AC impedance techniques.

The electrodes may be adapted to be immersed in a growth medium. The electrodes may be gold, silver chloride or carbon electrodes. The electrodes may be planar electrodes. The electrodes may be arranged for in vitro or in-vivo measurement.

The electrodes may be affixed to and/or at least part of an implantable device. The implantable device may be a cardiac stent, a metal heart valve or tissue valve attached to a metal affixing ting or stent, a vascular stent or a metallic surface of an implantable joint such as a hip joint.

The frequency range may preferably be any frequency range lying between 0.001 Hz and 33 MHz. Optionally the frequency range may be any frequency range above 0.001 Hz. In some applications, dc voltage or current for baseline and normalisation calculations may be used.

The system may be arranged to obtain a baseline impedance response over a frequency range.

The system may be arranged to obtain at least one measured impedance response over the frequency range. The at least one measured impedance response may include both real and imaginary parts of the impedance or may comprise only real or only imaginary parts of the impedance.

The system may be adapted to obtain the at least one normalized impedance response by dividing the at least one measured impedance response of the system at each frequency in the frequency range by the baseline impedance response of the system for the corresponding frequency.

According to a third aspect of the present invention is an implantable device comprising at least one electrode, the implantable device being adapted for use with the method of the first aspect and/or the system of the second aspect.

The implantable device may preferably be a stent, a prosthesis or a replacement organ and/or may optionally be any implantable medical device having a bare metal surface or that has had a metal surface introduced.

BRIEF DESCRIPTION OF THE DRAWINGS

Various aspects of the invention will now be described by way of example only with reference to the accompanying drawings, of which.

DETAILED DESCRIPTION OF THE DRAWINGS

Figure 1:
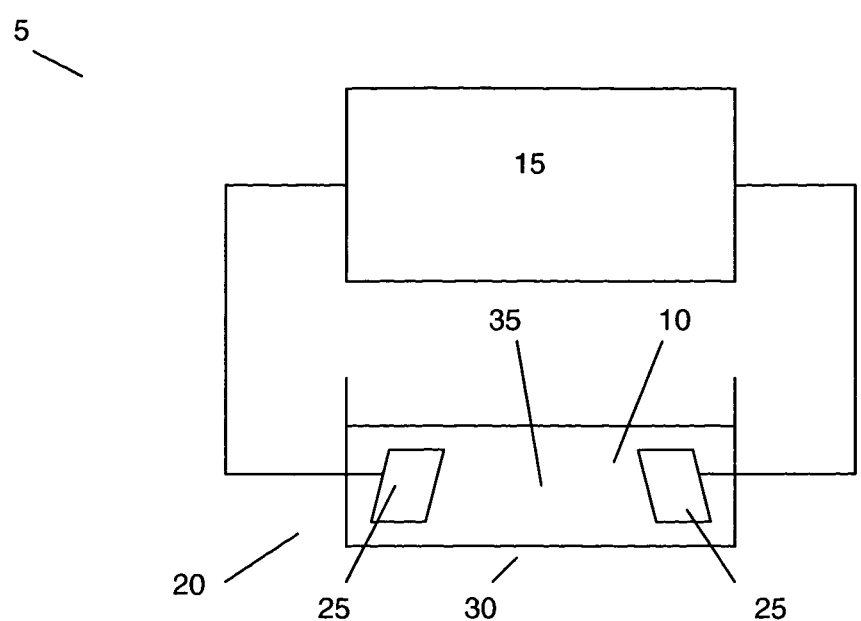
FIG. 1 is a system for characterising cells.

FIG. 1 shows an apparatus 5 for characterising biological cells 10, such as plant or animal cells, bacteria, plant or animal tissue, multicellular organisms, archaea and the like. The apparatus 5 comprises a controller 15 for providing an electrical signal to, and obtaining an electrical response from a measurement system 20 comprising two planar gold electrodes 25 located within a container 30 for holding growth medium 35. The growth medium 35 is conductive such that when the container 30 is filled, an electrical circuit is completed including the electrodes 25, the controller 15 and the growth medium 35.

The controller 15 is arranged to perform AC impedance spectroscopy by monitoring the impedance response of the system 20 to a small AC perturbation current over a range of frequencies. This involves applying an electrical stimulus between the electrodes 25 and measuring the magnitude and phase of the current and voltage between at least two points in the electrical path between them. In this case, the measurement points are at the electrodes 25 themselves. However, a skilled person would appreciate that alternate embodiments are possible wherein one or more additional measurement electrodes are used. The measured voltages and currents can be used to determine the impedance of the system and the magnitude and/or phase and/or phase difference of the impedance, voltage and/or current can be analysed to determine properties of the electrical circuit.

Figure 2:
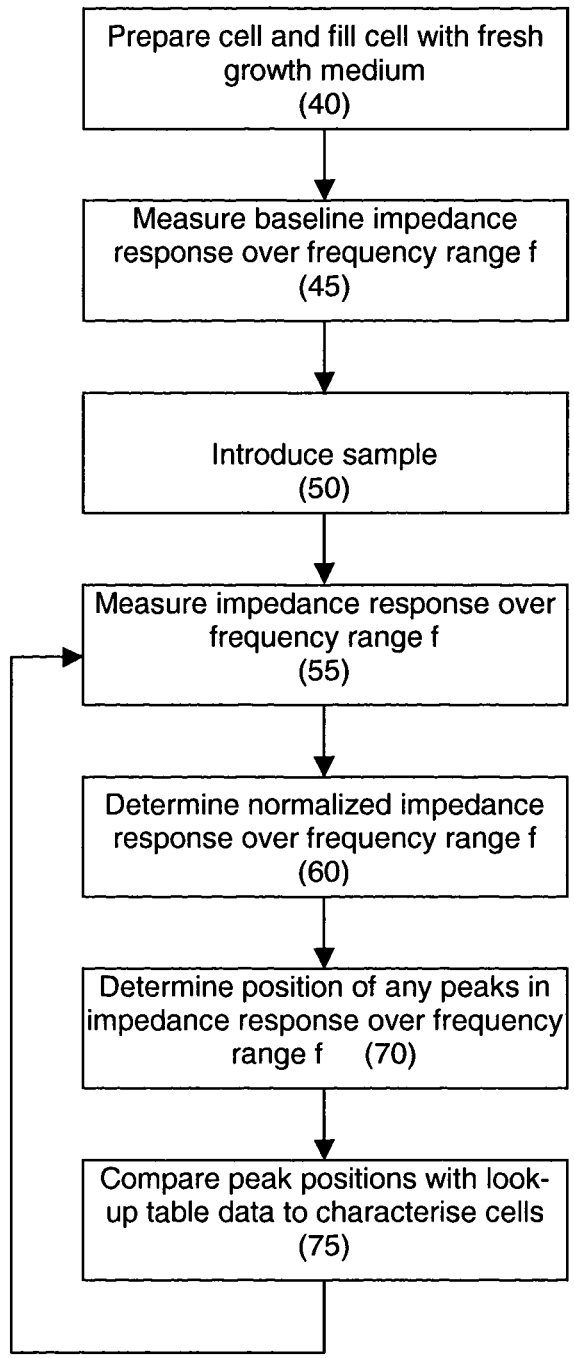
FIG. 2 is a flow diagram of a method for characterising cells.

A method of characterising cells located in the electrical path between the electrodes 25 is outlined in FIG. 2. Preparation for the characterisation, indicated at step 40, involves cleaning the electrodes 25 or providing fresh electrodes 25 in order to remove any contamination or oxidation from surfaces of the electrodes 25, which may otherwise lead to spurious results. The container 30 is then filled with a growth medium 35 suitable for growing the desired cells, such that the electrodes 25 are immersed in the growth medium 35. The growth medium 35 may be any suitable conductive and electrochemically stable growth medium known in the art.

The controller 15 is operable to carry out an AC impedance sweep of the system 20, measuring the impedance of the system 20 over a selected frequency range, f, in order to collect a baseline impedance response, $Z_{measured}(f,t=0)$, for that system 20 and frequency range, as indicated in step 45. The frequency sweep range, f, can be set to a range indicative of a cell or cells to be investigated or a broad sweep can be performed, for example, if the cell type or types are unknown or a wide range of cell types are being characterised. Typically, frequencies between 0.1 Hz and 32 MHz are suitable for characterising most cell types.

The swept frequency range can include one or more frequency sub-ranges, wherein each sub-range may be selected to investigate an expected impedance response. Further, although the measurement is carried out by collecting data for frequency spectra rather than an individual frequency, it will be appreciated that some apparatus, particularly digital apparatus, may collect a quasi-continuous frequency range by collecting a series of measurements at discrete frequencies, each frequency being separated by a frequency step. The frequency step is selected to be sufficiently small such that the series of discrete frequencies appears to be continuous. Alternatively, a continuous range can be obtained by interpolating the discrete points.

In some circumstances, the baseline impedance response may not be known, or collection of such data may be inconvenient. In these cases, it is possible to construct a similar or standard electrode system and obtain an approximation of the baseline impedance response $Z_{measured}(f,t=0)$. However, if the electrodes 25 are implanted or part of an implanted/in-vivo system, then it is preferable to collect a baseline impedance response in situ, due to the complexity of the growth medium and electrode arrangement, which may be difficult to approximate.

Once collected or approximated baseline data has been obtained, then the cells to be analysed are introduced and/or grown in the growth medium in step 50. In step 55, the controller 15 is then operable to carry out at least one further AC impedance sweep of the system 20, measuring the impedance of the system 20 over the selected frequency range, f, in order to collect at least one measured impedance response, $Z_{measured}(f,t)$.

The measured impedance response $Z_{measured}(f,t)$ for the frequency range is then divided by the corresponding baseline impedance response $Z_{measured}(f,t=0)$ for the frequency range to obtain the normalized frequency, $Z_n(f,t)$, in step 60. For embodiments where the impedance response is measured as a quasi-continuous series of impedance values at discrete frequencies, the measured impedance response for each discrete frequency in the frequency range is divided by the baseline impedance response for that frequency.

For dynamic systems, where the cell composition or type is changing or where cells 10 are growing and/or multiplying in the growth medium 35, the measured impedance response $Z_{measured}(f,t)$ can be redetermined and the cells 10 recharacterised at regular time intervals. In this way, the evolution of the cells within the system over time can be monitored.

Figure 3:
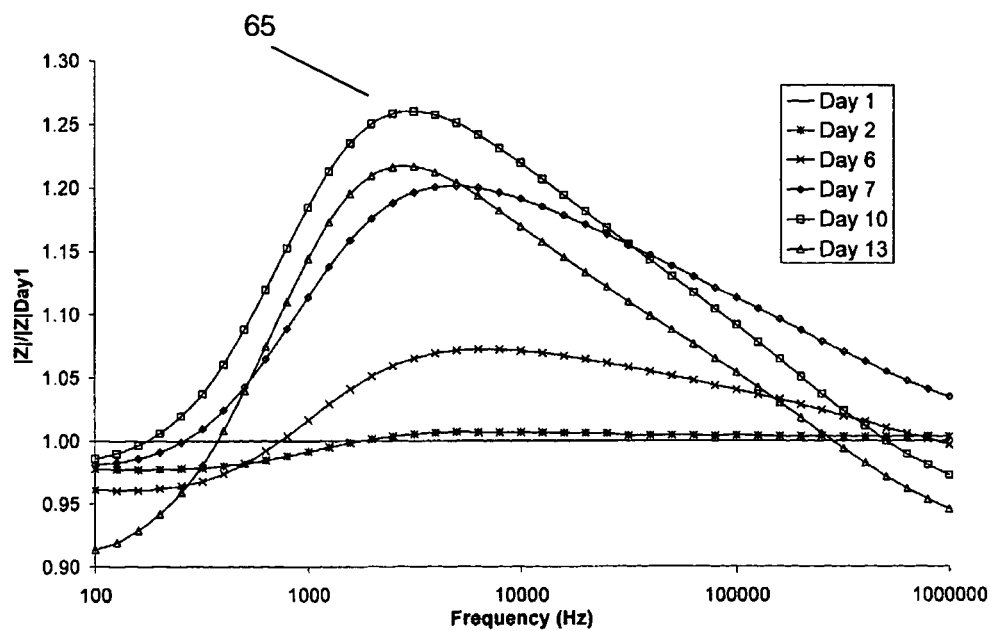
FIG. 3 shows the frequency response of the normalised impedance of smooth muscle cells obtained using the system of FIG. 1 and the method of FIG. 2.

The change of the frequency dependence of normalised impedance over time with growth of smooth cardiac muscle cells is shown in FIG. 3. It can be seen from this that a peak 65 in the normalised impedance appears as the cardiac cell culture grows. At confluence, i.e. when the electrodes are covered by cells, the peak characteristic of this type of cell can be seen to occur at just under 3000 Hz.

Without wishing to be bound by any particular theory, it is likely that the peak 65 is due to individual cell 10 components contributing to the resistance and capacitance of the system 20 and to interactions between the cell culture and the electrodes 25. Some small amounts of inductance may also contribute to the response.

By determining the frequency at which the peaks 65 occur the cells 10 in step 70 can be characterised. Alternatively, more advanced techniques such as model fitting, magnitude of the normalised impedance and peak fitting may be used. The peak positions can be compared with characteristic peak positions stored in a look up table in order to identify cell type. Optionally, equivalent circuit analysis can be used instead of peak fitting. Equivalent circuit analysis can yield values for cell or bacteria resistance and capacitance that are characteristic of the organism and/or its stage of growth.

Figure 4:
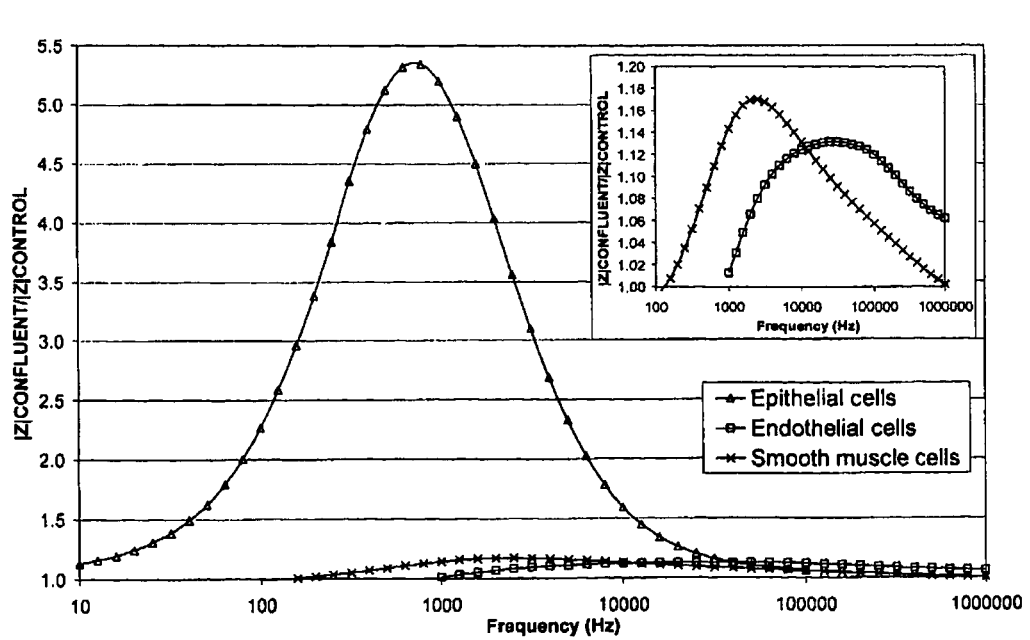
FIG. 4 shows the frequency response of the normalised impedance of smooth muscle cells, epithelial cells and endothelial cells obtained using the system of FIG. 1 and the method of FIG. 2.

To demonstrate the ability of this technique to differentiate between cell types, the above method was repeated separately for epithelial cells and endothelial cells. As can be seen from the results, as shown in FIG. 4, at confluence, the frequency response of normalised impedance for epithelial cells peaks at approximately 1000 Hz, the peak for smooth muscle cells is closer to 2000 Hz whilst the peak for endothelial cells is closer to 20000 Hz. In this way, when faced with three unknown cell types, the apparatus and method as described above are able to characterise the cell type based on the position of characteristic peaks in the frequency response of the normalised impedance at confluence.

Figure 5:
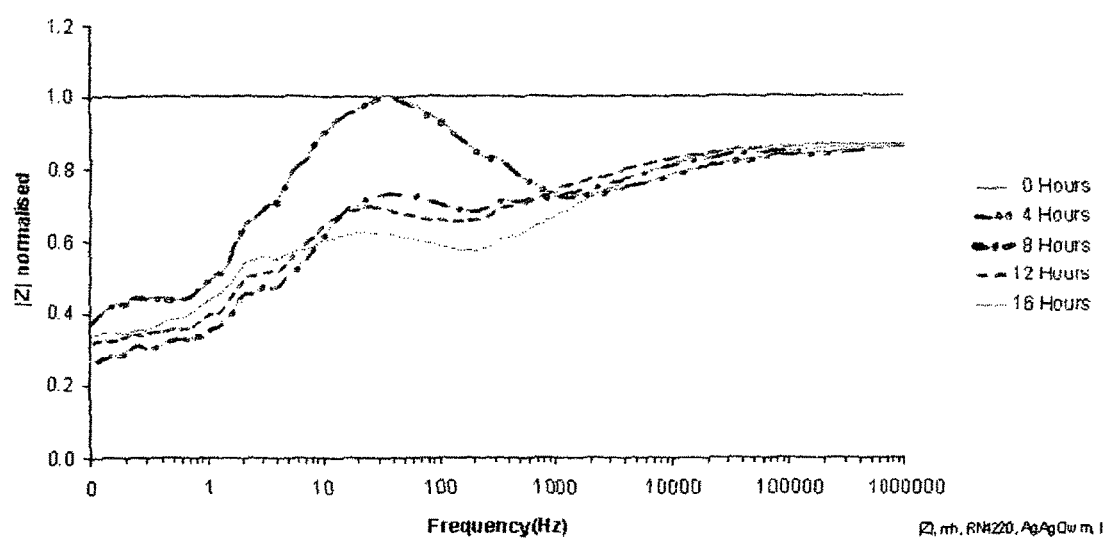
FIG. 5 shows the frequency response of the normalised impedance of staphylococcus aureus bacteria obtained using the system of FIG. 1 and the method of FIG. 2.

The utility of this technique lies not only in characterisation of tissue cells, but surprisingly it can also be used to characterise other cell types and cellular organisms. As an example, the above cell characterisation method was applied to a staphylococcus aureus bacteria culture in a bacterial broth growth medium. As can be seen from the resulting normalised impedance spectrum, as shown in FIG. 5, a number of peaks in normalised impedance are obtained at certain characteristic frequencies. These peaks are useable to characterise the bacteria in question. Each curve is characteristic of the type of bacteria and stage of growth.

In an embodiment of the present invention, at least the electrodes 25 can be incorporated on or in, or form at least part of, an implantable device. The implantable device may be a dedicated sensor, or alternatively, the implantable device can be a medical implant or prosthesis, such as a stent, or a replacement organ or part of an organ such as a heart valve. In this way, the environment and condition of the implantable device can be monitored. For example, the degree of restinosis forming around a stent can be detected and quantified or the formation of scar tissue around an implant can be determined or bacterial infection within the body may be identified. In another example, if the electrode system is placed within a wound dressing close to the surface of a wound, it can be used to signal both the presence of a bacterial infection and the type of bacteria. It can also be seen that such a system could be employed in a small instrument for use in characterising cell cultures, or used as an instrument for characterising wound swabs or surface swabs in the laboratory.

A skilled person will appreciate that variations of the disclosed arrangements are possible without departing from the scope of the invention. For example, although the apparatus 5 described above uses gold electrodes 25, it will be appreciated that other materials, such as platinum, may be used. The above method and apparatus may be applied to a range of applications such as determining the degree of restenosis, in body scientific investigations, detection of chemical materials, calcification, etc. Although a two electrode 25 system having a working electrode and a counter electrode is described, it will be appreciated that other electrode arrangements, such as at least one additional measurement electrode, may be used. Although the electrodes 35 described above are planar, it will be appreciated that other conformations of electrode may be used, particularly if an electrode 25 is incorporated into an implantable device, wherein the electrodes 25 may be conformed to the shape of the device. Although the control unit 15 and the electrodes 25 are described as being directly coupled through wires, it will be appreciated that other coupling means may be provided, such as inductive coupling or wireless coupling, particularly for implantable in-vivo devices.

The invention claimed is:

1. A method for characterizing unidentified cells or cell structures in a sample, said method comprising:
   implanting at least a portion of a device within a subject containing the sample, the device comprising a controller and at least two electrodes;
   monitoring, via the controller, at least one characteristic of the sample located in an electrical path between the electrodes;
   obtaining, via the controller and utilizing the at least two electrodes, at least one normalized impedance response of the sample over at least one frequency range, wherein the normalized impedance is a measured impedance divided by a baseline impedance, wherein the measured impedance comprises at least one of a real or an imaginary part, and wherein the baseline impedance is an impedance response of the sample over the at least one frequency range with substantially no cells in an electrical path between at least two electrodes;
   identifying, via the controller and within a set of data containing a plurality of normalized impedance responses associated with a corresponding plurality of cell types, at least one characteristic of the normalized impedance response over the at least one frequency range that is indicative of a single cell type within the plurality of cell types; and
   characterizing, via the controller, at least one unidentified cell to determine cell identity by using the identified at least one characteristic of the normalized impedance response over the at least one frequency range,
   wherein:
      the determined cell identity is characteristic of at least a cell type and a stage of growth of the at least one unidentified cell in the sample; and
      the at least one characteristic of the normalized impedance response used for characterizing the at least one unidentified cell is at least one of a number of peaks in the normalized impedance.

2. A method according to claim 1, wherein the frequency range is a continuous or quasi-continuous frequency range or spectrum.

3. A method according to claim 1, wherein the frequency range comprises a series of discrete frequency measurements.

4. A method according to claim 1, wherein the frequency range is any frequency range lying between 0.1 Hz and 33 MHz.

5. A method according to claim 1, wherein at least one of:
the at least one cell is a bacteria or other single cell organism;
the at least one cell is a plant or animal cell such as a plant or animal tissue cell;
at least one cell is arranged in a structure, such as plant or animal tissue or a multi-cell organism.

6. A method according to claim 1, wherein the baseline impedance response is at least one of an initial or a calculated or estimated or standard impedance response of the system.

7. A method according to claim 6, wherein the baseline impedance response of the system is further based at least in part upon measurement of an impedance response of at least one of a similar or a standardised system over the at least one frequency range with substantially no cells in an electrical path between at least two electrodes.

8. A method according to claim 1, wherein the at least one measured impedance response of the system over the at least one frequency range is obtained after at least one of introduction or growth of at least one cell in the electrical path between at least two electrodes.

9. A method according to claim 1, wherein the at least one characteristic of the normalized impedance response is further at least one of the frequency, the peak size, or the peak shape of at least one peak in the normalized impedance response over the frequency range.

10. A method according to claim 9, wherein at least the at least one peak is used to determine the stage of growth of at least one cell or bacterial system.

11. A method according to claim 10, wherein changes in at least one peak in the normalized system are tracked over time to allow the distinction of changes in cell or bacterial growth.

12. A method according to claim 9, wherein the at least one peak in normalized impedance with frequency is characteristic of at least one of cell or bacterial type or growth stage and the normalized impedance is used to determine the presence of a particular cell, bacteria, tissue type, or molecular by-product in the system.

13. A method according to claim 1, wherein at least two electrodes used to obtain the normalized impedance response are immersed in a culture medium.

14. A method according to claim 13, wherein the culture medium is arranged to promote the growth of at least one type of cells.

15. A method according to claim 1, wherein the measurement of at least one of the impedance response of the system, the baseline impedance response of the system, or the normalized Impedance response of the system is made using AC impedance techniques.

16. The method according to claim 1, further comprising the steps of applying an electrical stimulus between the at least two electrodes and measuring a magnitude and phase of a current and a voltage between at least two points in the electrical path between the electrodes.

17. A method for characterizing unidentified cells or cell structures in a sample, said method comprising:
positioning a device within a dressing positioned adjacent a surface of a wound on a subject containing the sample, the device comprising a controller and at least two electrodes;
monitoring, via the controller, at least one characteristic of the sample located in an electrical path between the electrodes;
obtaining, via the controller and utilizing the at least two electrodes, at least one normalized impedance response of the sample over at least one frequency range, wherein the normalized impedance is a measured impedance divided by a baseline impedance, wherein the measured impedance comprises at least one of a real or an imaginary part, and wherein the baseline impedance is an impedance response of the sample over the at least one frequency range with substantially no cells in an electrical path between at least two electrodes;
identifying, via the controller and within a set of data containing a plurality of normalized impedance responses associated with a corresponding plurality of cell types, at least one characteristic of the normalized impedance response over the at least one frequency range that is indicative of a single cell type within the plurality of cell types; and
characterizing, via the controller, at least one unidentified cell to determine cell identity by using the identified at least one characteristic of the normalized impedance response over the at least one frequency range,
wherein:
the determined cell identity is characteristic of at least a cell type and a stage of growth of the at least one unidentified cell in the sample; and
the at least one characteristic of the normalized impedance response used for characterizing the at least one unidentified cell is at least one of a number of peaks in the normalized impedance.

18. The method according to claim 17, wherein the frequency range is a continuous or quasi-continuous frequency range or spectrum.

19. The method according to claim 17, wherein the frequency range comprises a series of discrete frequency measurements.

20. The method according to claim 17, wherein the baseline impedance response is at least one of an initial or a calculated or estimated or standard impedance response of the system.

21. The method according to claim 20, wherein the baseline impedance response of the system is further based at least in part upon measurement of an impedance response of at least one of a similar or a standardised system over the at least one frequency range with substantially no cells in an electrical path between at least two electrodes.

22. The method according to claim 17, wherein:
the at least one characteristic of the normalized impedance response is further at least one of the frequency, the peak size, or the peak shape of at least one peak in the normalized impedance response over the frequency range;
at least the at least one peak is used to determine the stage of growth of at least one cell or bacterial system; and
changes in at least one peak in the normalized system are tracked over time to allow the distinction of changes in cell or bacterial growth.

23. The method according to claim 17, further comprising the steps of applying an electrical stimulus between the at least two electrodes and measuring a magnitude and phase of a current and a voltage between at least two points in the electrical path between the electrodes.

* * * * *